United States Patent
Bani-Hashemi (10) Patent No.: US 8,238,519 B2
(45) Date of Patent: Aug. 7, 2012

(54) ROTATIONAL RADIATION TREATMENT OF MOVING TARGETS

(75) Inventor: Ali-Reza Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 203 days.

(21) Appl. No.: 12/834,067

(22) Filed: Jul. 12, 2010

(65) Prior Publication Data

US 2012/0008744 A1   Jan. 12, 2012

(51) Int. Cl.
*A61N 5/10* (2006.01)

(52) U.S. Cl. ......................................................... 378/65

(58) Field of Classification Search .................. 378/62, 378/65, 95, 145, 147, 150, 151
See application file for complete search history.

(56) References Cited

U.S. PATENT DOCUMENTS

| | | |
|---|---|---|
| 5,818,902 A | 10/1998 | Yu |
| 7,469,035 B2 | 12/2008 | Keall et al. |
| 7,609,810 B2 | 10/2009 | Yi et al. |
| 7,983,380 B2* | 7/2011 | Guertin et al. .............. 378/4 |
| 2005/0054916 A1 | 3/2005 | Mostafavi |
| 2008/0226030 A1 | 9/2008 | Otto |
| 2008/0243018 A1 | 10/2008 | Zuhars et al. |
| 2009/0041200 A1 | 2/2009 | Lu et al. |
| 2010/0183120 A1 | 7/2010 | Nord et al. |
| 2010/0189220 A1* | 7/2010 | Flynn et al. ................. 378/65 |
| 2010/0329422 A1* | 12/2010 | Brown et al. ................ 378/65 |
| 2011/0080990 A1* | 4/2011 | Filiberti et al. .............. 378/4 |
| 2011/0200170 A1* | 8/2011 | Nord et al. .................. 378/65 |

FOREIGN PATENT DOCUMENTS

| | | |
|---|---|---|
| GB | 2 441 550 | 3/2008 |
| WO | WO 2007/012185 | 2/2007 |

OTHER PUBLICATIONS

Oliver, et al., *Experimental measurements and Monte Carlo simulations for dosimetric evaluations of intrafraction motion for gated and ungated intensity modulated arc therapy deliveries; IMAT deliveries with motion management*, Physics in Medicine and Biology, Taylor and Francis Ltd., London, GB, vol. 53, No. 22, Nov. 21, 2008, pp. 6419-6436, XP020141511, ISSN 0031-9155, DOI: 10.1088/0031-9155/53/22/010.

EP Search Report in EP application No. EP 11 17 3380, dated Oct. 18, 2011, 10 pages total.

EP Search Report in counter EP application No. EP 11 17 3319, dated Oct. 25, 2011, 7 pages total. Silke Ulrich et al., "Development of an optimization concept for arc-modulated cone beam therapy", Physics in Medicine and Biology, 52 (2007), IOP Publishing, doi:10.1088/0031-9155/52/14/2006, (pp. 4099-4119, 21 pages total).

Cedric X. Yu, "Intensity Modulated Arc Therapy: Technology and Clinical Implementation", AbstractID: 10351 Title: Advances in arc therapy, 14pgs.

* cited by examiner

*Primary Examiner* — Irakli Kiknadze (57) ABSTRACT

Some aspects include a system, apparatus, and method for determining that a motion of a patient area of a patient due to breathing is substantially periodic according to a treatment plan, moving a radiotherapy gantry towards a first treatment gantry angle, moving a radiotherapy beam shaping device towards a first treatment shape corresponding to the first treatment gantry angle, determining when a next treatment window is to begin based on a predictive model derived from the motion of the patient area, where the treatment window is a period of time designated for delivery of treatment radiation to the patient area according to the treatment plan, adjusting the moving of the radiotherapy gantry such that the radiotherapy gantry will reach the first treatment angle during the determined next treatment window, and delivering a treatment radiation beam to the patient area during the determined next treatment window.

18 Claims, 7 Drawing Sheets

ROTATIONAL RADIATION TREATMENT OF MOVING TARGETS

BACKGROUND

1. Field

The embodiments described below relate generally to delivery of radiotherapy treatment. More specifically, some embodiments are directed to rotational radiation treatment of moving patient areas and systems for delivering such treatments.

2. Description

Radiotherapy or radiation therapy is used to treat cancer and other diseases with ionizing radiation. Conventional radiotherapy systems generate and direct a beam of radiation to a targeted treatment area within a patient volume. The radiation beam is intended to injure or destroy cells within the targeted area by causing ionizations within the cells or other radiation-induced cell damage.

Radiotherapy treatment plans for delivering radiation to a patient are intended to maximize radiation delivered to a targeted area, while minimizing the radiation delivered to healthy tissue. In this regard, the treatment of a moving target area poses a challenge to radiotherapy. In the context of rotational radiotherapy treatments, the treatment of moving targets is further complicated due to the movement of the gantry in one or more arcs around the patient. Such rotational radiotherapies include but are not limited to Arc-Modulated ConeBeam Therapy, Intensity Modulated Arc Therapy, and a variety of other radiotherapy treatment schemes that involve rotating a linear accelerator (LINAC) gantry about the patient and delivering radiation to a targeted patient area from a number of different gantry angles. In some contexts, the delivery of the treatment radiation may be either continuous or at discrete locations.

One conventional method for addressing the delivery of radiation treatment to moving targets includes using an increased margin of delivery around a target that is large enough to account for target excursions from a nominal position. While the increased margin may result in the target receiving a desired radiation dose, surrounding healthy tissue or organs are at an increased risk of also receiving radiation. Gated treatment techniques to address moving targets involve determining a gating window during which the target movement is minimized to deliver the radiation treatment. For example, radiation may be delivered to the target only when the patient is within 80% exhalation of the breathing cycle, a period when motion of the targeted treatment area may be relatively motionless. However, acquisition of planning images (e.g., 4D CT computed tomography) and a breathing monitoring device to provide an indication of the phases of the patient's breathing cycle are needed for this technique. One proposed technique for delivering radiation to a moving target involves using an auxiliary device to determine the location and the shape of the target at any point in time and reshaping the MLC (multileaf collimator) leaves of the radiotherapy system to follow (i.e., track) the target shape at any point in time. However, this technique also requires an auxiliary device in addition to the radiotherapy system.

The present inventors have realized that conventional rotational radiation treatments are inefficient and insufficient for rotational radiotherapy treatment of moving targets. Accordingly, other methods and systems to provide rotational radiation treatment of moving target areas are desired.

SUMMARY

In order to address the foregoing, some embodiments provide a system, method, apparatus, and means to determine a motion of a patient area due to breathing is substantially periodic according to a treatment plan, wherein the treatment plan specifies a first treatment gantry angle at which a prescribed dose of radiation is to be delivered, a nominal time between consecutive breaths of the patient, and a gantry travel time during which a radiotherapy beam shaping device is configured for delivery of the prescribed dose of radiation and is equal to the nominal time between consecutive breaths of the patient, move a radiotherapy gantry towards the first treatment gantry angle, move the radiotherapy beam shaping device towards a first treatment shape corresponding to the first treatment gantry angle, according to the treatment plan, and to determine when a next treatment window is to begin based on a predictive model derived from the motion of the patient area, the treatment window being a period of time designated for delivery of a treatment radiation beam to the patient area according to the treatment plan. Such methods and systems further provide adjusting the moving of the radiotherapy gantry such that the radiotherapy gantry will reach the first treatment angle during the determined next treatment window and delivering a treatment radiation beam to the patient area during the determined next treatment window, wherein the radiotherapy gantry is at the first treatment gantry angle and the radiotherapy shaping device is configured to the first treatment shape.

According to some aspect, some embodiments may include receiving, obtaining, or processing the treatment plan.

According to some embodiments, the radiotherapy gantry is continuously moving. In some aspects a speed of the moving of the radiotherapy gantry towards the first treatment gantry angle depends, at least in part, on a rate at which the radiotherapy beam shaping device can be configured to the first treatment shape. Other, additional, or fewer factors may be considered in determining whether the treatment radiation will be delivered to a patient area. In some aspects, such considerations may include determining the radiotherapy beam shaping device is configured to the first treatment shape corresponding to the first treatment gantry angle, determining the radiotherapy gantry has reached the first treatment gantry angle according to the treatment plan, and determining the radiotherapy gantry will reach the first treatment angle during the determined next treatment window.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
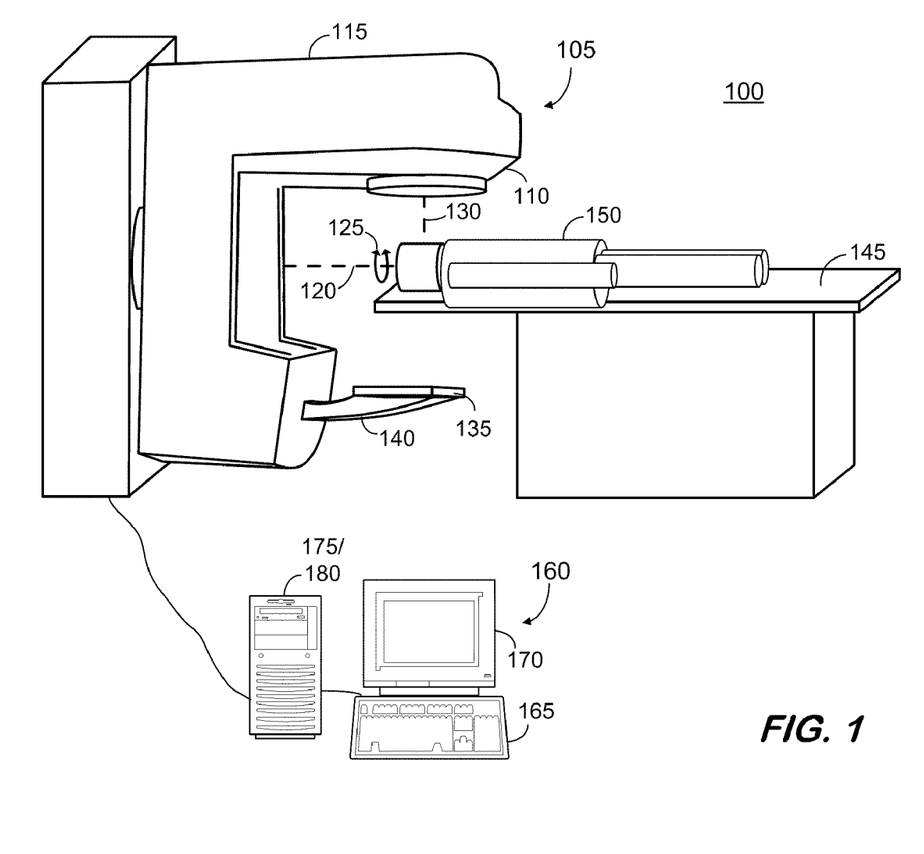
FIG. 1 is a perspective view of a treatment room according to some embodiments.

FIG. 1 illustrates radiotherapy treatment room 100 pursuant to some embodiments. Radiotherapy treatment room 100 includes linear accelerator (linac) 105, table 145 and operator console 160. The various components of radiotherapy treatment room 100 may be used to deliver a beam of radiation to a beam object such as patient 150. The patient may be positioned to receive the beam according to a radiation treatment plan. The elements of treatment room 100 may be employed in other applications according to some embodiments.

Linac 105 generates and emits a radiation beam (e.g., an x-ray beam) from treatment head 110. The radiation beam may comprise electron, photon or any other type of radiation. According to some embodiments, the beam exhibits energies in the megavoltage range (i.e. >1 MeV) and may therefore be referred to as megavoltage beam.

Treatment head 110 is coupled to a projection of gantry 115. Gantry 115 is controllable to be rotatable around gantry axis 120. As indicated by arrow 125, gantry 115 may rotate clockwise or counter-clockwise according to some embodiments. Rotation of gantry 115 serves to rotate treatment head 110 around axis 120.

During radiation emissions (e.g., treatment, imaging, calibration, and other procedures) treatment head 110 emits a divergent beam of megavoltage x-rays along beam axis 130. The beam is emitted towards the isocenter of linac 105. The isocenter may be located at the intersection of beam axis 130 and gantry axis 120. Due to divergence of the beam and the shaping of the beam by beam-shaping devices in treatment head 110, the beam may deliver radiation to a volume of patient 150 rather than only through the isocenter.

Table 145 may support a patient during radiation treatment and other aspects discussed herein. Table 145 may be adjustable to assist in positioning patient 150 or a particular target area and volume of the patient at the isocenter. Table 145 may also be used to support devices used for such positioning, for calibration and/or for verification.

Imaging device 135 may comprise any system to acquire an image based on radiation received at the imaging device. Imaging device 135 may be attached to gantry 115 in any manner, including an extendible and retractable housing 140. Rotation of gantry 115 may cause treatment head 110 and imaging device 135 to rotate around the isocenter such that the isocenter remains located between treatment head 110 and imaging device 135 throughout stationary and rotational movements of gantry 115.

Imaging device 135 may acquire projection images before, during and/or after radiation treatment. In some embodiments, imaging device 135 may include an analog or a digital radiation detector. Imaging device 135 may be used to acquire images based on radiation emitted from treatment head 110. These images may reflect the attenuative properties of objects located between treatment head 110 and imaging device 135. Such projection images may be used to determine imaging geometry parameters associated with the imaging system comprising treatment head 110 and imaging device 135. The two-dimensional projection images and/or three-dimensional images reconstructed based on the projection images may be used to detect, monitor, and record a target area or volume (e.g., a tumor) position and a movement of the target area or volume.

Operator console 160 includes input device 165 for receiving instructions from an operator such as an instruction to calibrate linear accelerator 105 and an instruction to configure the beam shaping device of treatment head 110 (e.g., a collimator) with a particular field of view for a particular interval of time. Console 160 also includes output device 170 that may include a monitor for presenting acquired three-dimensional images, operational parameters of linear accelerator 105 and/or interfaces for controlling elements thereof. Input device 165 and output device 170 are coupled to processor 175 and storage 180.

Processor 175 executes program code according to some embodiments. The program code may be executable to control linear accelerator 105 to operate as described in various methods and processes herein. The program code may be stored in storage 180, which may comprise one or more storage media of identical or different types, including but not limited to a fixed disk, a floppy disk, a CD-ROM, a DVD-ROM, an optical disk, a magnetic tape, a solid state storage device, a flash drive, and a signal. Storage 180 may store, for example, initial imaging geometry parameters, radiation treatment plans, projection images, software applications to calibrate linear accelerator 105 and/or to provide radiation treatment, and other data used to perform radiation treatment.

Operator console 160 may be located apart from linear accelerator 105, such as in a different room, in order to protect its operator from radiation. For example, linear accelerator 105 may be located in a heavily shielded room, such as a concrete vault, which shields the operator from radiation generated by accelerator 105.

Each of the devices shown in FIG. 1 may include fewer or more elements than those shown and are not limited to the devices shown in FIG. 1.

Figure 2:
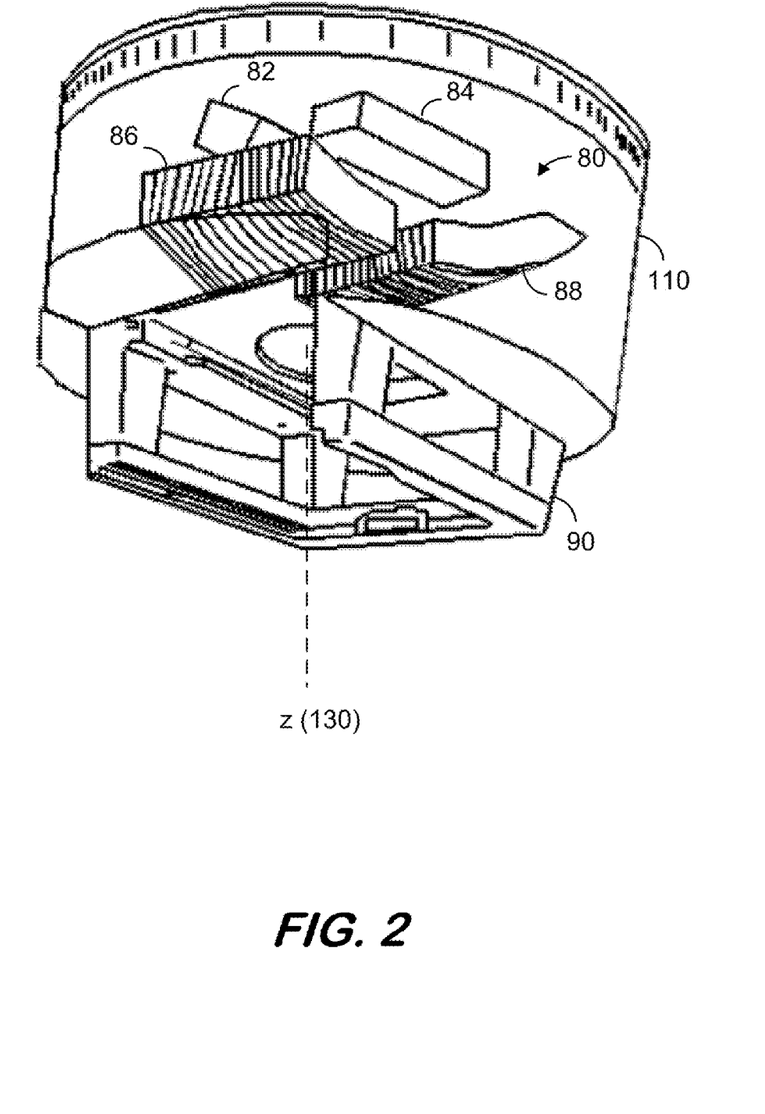
FIG. 2 is a depiction of a beam shaping device in accordance with some embodiments.

FIG. 2 illustrates treatment head 110 according to some embodiments. Treatment head 110 includes a beam shaping device, collimator 80, that may be used to shape a radiation beam to conform to an aperture specified by a treatment plan. Collimator 80 includes a pair of jaws (Y-jaws) 82 and 84 and a pair of jaws (X-jaws) 86 and 88. The positioning of X-jaws 86 and 88 and Y-jaws 82 and 84 determines a size and shape of an opening (i.e, a field of view) through which a radiation beam may pass along axis 130.

Each pair of jaws 86/88 and 82/84 is rotatable about axis 130. As depicted in FIG. 2, X-jaws 86 and 88 may be formed of a plurality of individual elements. These individual elements may be movable along a path intersecting axis 130. Movement of each element may be individually controllable to generate a wide variety of aperture shapes.

Treatment head 110 also includes accessory tray 90. Accessory tray 90 may be configured to receive and securely hold attachments used during the course of treatment planning and treatment (such as, for example, reticles, wedges, or the like). According to some embodiments, treatment head 110 is rotatable to rotate collimator 80 and accessory tray 90 around axis 130 while maintaining the physical relationships between X-jaws 86 and 88, Y-jaws 82 and 84, and accessory tray 90.

Effective treatment of moving targets includes detecting and monitoring the motion of a target area, and delivering radiotherapy beams to the moving target. A number of conventional technologies may be used to detect and monitor target motion. Some techniques include providing a device to monitor the rise and fall of an external surface of the patient caused by breathing. Such devices may include a belt that holds a strain-gauge against a patient's moving chest and/or abdomen, wherein the strain-gauge produces a signal corresponding to the rise and fall of the patient's chest/abdomen. Some other techniques include optical mechanisms that monitor external fiducial markers attached to the patient's skin and produce a signal corresponding to the rise and fall of the patient's chest/abdomen. Some other techniques include providing implantable beacon devices in a patient to directly monitor and detect tumor motion without a surrogate. Further technologies for monitoring the motion of a patient area targeted for radiotherapy treatment include using real-time imaging based systems such as, for example, fluoroscopy imaging systems and magnetic resonance (MR) imaging systems.

In some embodiments, radiotherapy planning for rotational radiation treatment of a moving target includes gate-acquisition computed tomography (CT) imaging to monitor the motion of the breathing of a patient that is to receive rotational radiation treatment. The CT acquisition may be performed in a variety of manners, including processes now known and those that become known in the future. In some aspects, the CT images may be acquired using a breath-hold at a particular phase of the breathing cycle that is deemed acceptable for radiation treatment purposes (e.g., at maximum exhale of the breathing cycle). In some aspects, four-dimensional CT (4D CT) acquisition that provides a CT volume of each phase of the breathing may be used to monitor the motion of the patient area, where the breathing cycle is divided into a number of phases (e.g., 10-16 phases). Based on the acquired images, a treatment planning clinician may decide during which phase(s) of the breathing the treatment radiation should be delivered to the patient. In another aspect, a respiratory device may be configured to acquire a CT volume only at a specific phase of the breathing cycle, such as maximum exhale.

In accordance with aspects herein, a CT volume of the targeted patient area may be acquired in a state, phase or portion of the breathing or other periodic motion of the patient area that is determined to be appropriate for the delivery of the treatment radiation. This acquired CT data may be used as a basis for the development of a radiotherapy treatment plan.

Figure 3:
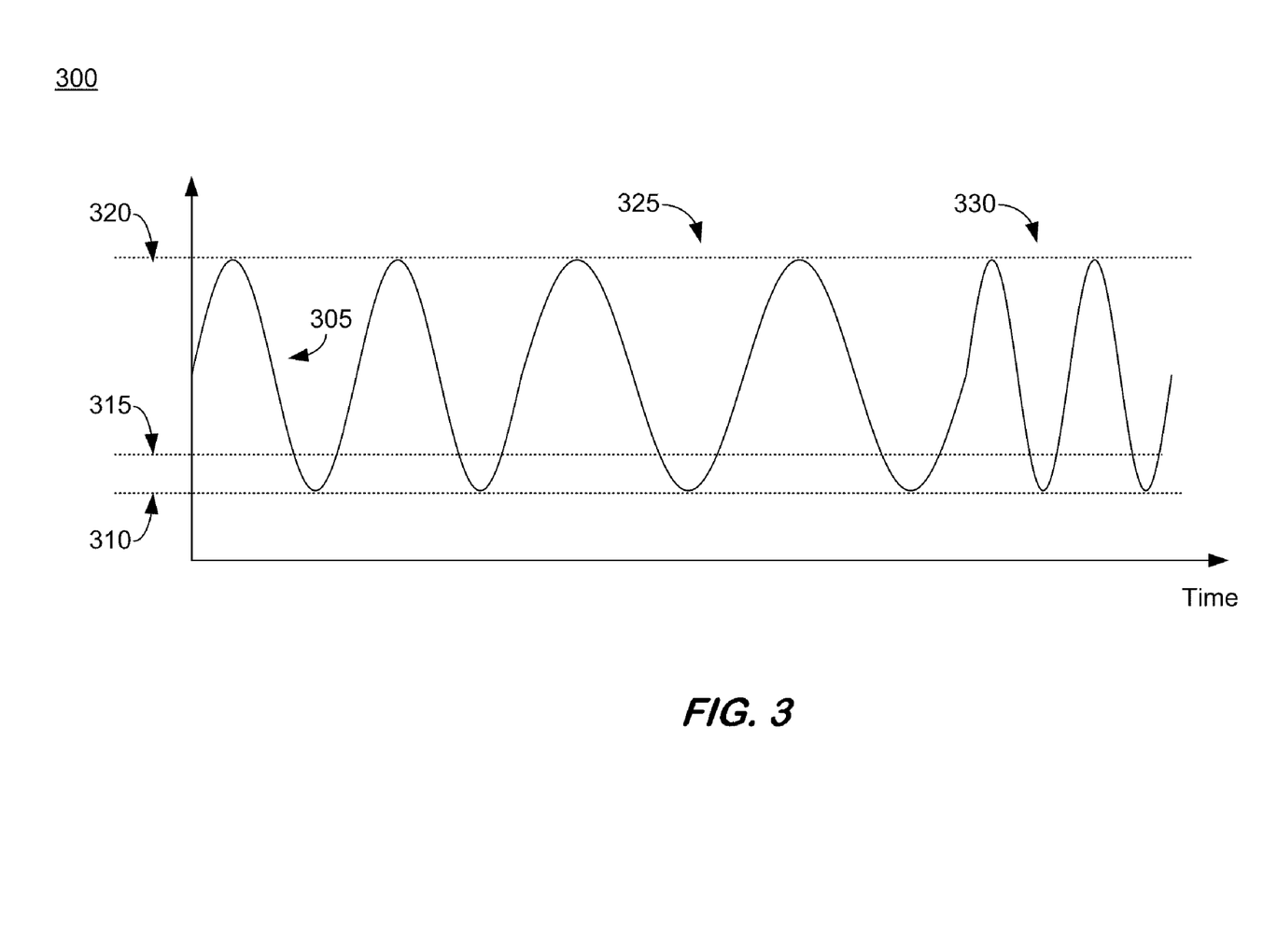
FIG. 3 is an illustrative depiction of a respiratory signal of a patient.

FIG. 3 provides an illustrative example of a respiratory signal 305, in accordance with some embodiments herein. While respiratory signal 305 is hypothetical, it is representative of a respiratory monitoring signal that may be derived from CT images and volumes and/or other data of a patient acquired during a radiotherapy treatment planning process and/or radiation treatment. Respiratory signal 305 illustrates a plurality of breathing cycles, wherein the breathing cycles vary between 100% exhalation at line 310, 80% exhalation at line 315, and 100% inhalation at line 320 over a period of time. It is noted that the time interval between 80% exhalation and 100% exhalation may be specified as the portion or phase of the breathing cycle for delivery of radiation treatment due to the relatively static motion a patient area may experience during this phase of the breath cycle, however embodiments are not thus limited. The period of time designated for delivery of treatment radiation is referred to herein as a treatment window. In the example of FIG. 3, the treatment window corresponds to the time period the breathing cycle is between 80% and 100% exhalation. In some aspects, the treatment window is selected based on, at least in part, the targeted patient area having an acceptable magnitude of motion. The acceptable magnitude of motion is preferably low so as not to compromise the radiotherapy treatment goals.

As shown, the breathing is slower at region 325 than the breathing depicted at region 330. Such variances of the periodic breathing, and thus a patient area movement, may be accounted for in some embodiments herein.

Figure 4:
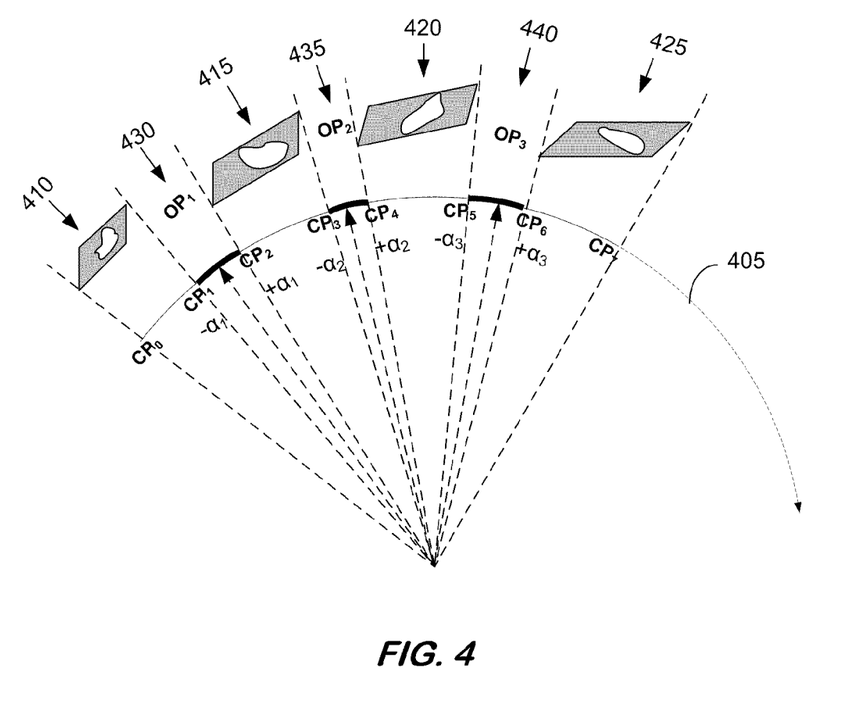
FIG. 4 is a depiction of some aspects of rotational radiation dose delivery according to some embodiments.

FIG. 4 is an illustrative depiction of some aspects of rotational radiation dose delivery according to some embodiments. More particularly, FIG. 4 illustrates various aspects of a treatment plan that may be used for delivery of rotational radiation treatment herein.

Arc 405 represents a path gantry 115 may traverse as the gantry rotates about a patient. In some aspects, treatment head 115 may deliver radiation to a patient area or volume of the patient, in accordance with a treatment plan, as gantry 115 rotates about the patient. In some embodiments, a treatment plan devised for treating patient 150 by rotational radiation delivered by radiotherapy system 100 specifies a finite number of discrete control points (CPs) on arc 405. Rotational radiation treatment scheme 400 includes a plurality of representative CPs—CP0, CP1, CP3, CP4, CP5, CP6. Since gantry 115 continuously moves through arc 405 according to some embodiments herein, gantry 115 moves through the CPs without stopping at the CPs.

The treatment plan for treating patient 150 by rotational radiation delivered by radiotherapy system 100 also specifies a finite number of discrete optimization points (OPs) on arc 305. Rotational radiation treatment scheme 400 includes a plurality of representative OPs, e.g., OP1 at 430, OP2 at 435, and OP3 at 440. In some embodiments, each OP represents a treatment gantry angle at which a prescribed dose amount of radiation is to be delivered to the patient area, as specified by a treatment plan. Since gantry 115 continuously moves in a rotational manner around the patient according to some embodiments herein, gantry 115 moves through the OPs without stopping at the OPs. In some aspects, the treatment radiation is delivered around each OP since gantry 115 moves continuously. Radiation dose delivery may occur around OP by delivering the radiation ($\pm\alpha$) each gantry treatment angle. This aspect of the treatment plan and radiation delivery scheme is illustrated in FIG. 4. In some embodiments, ($\pm\alpha$) may vary from OP to OP. As illustrated in FIG. 4, $OP_1$ (430) includes ($\pm\alpha_1$), $OP_2$ (435) includes ($\pm\alpha_2$), and $OP_3$ (440) includes ($\pm\alpha_3$)To make it more general, let's add that $\pm\alpha$ may vary from OP to OP. It would be better to illustrate in FIG. 4 that each OP has its distinct $\pm\alpha$. $OP_1$ will correspond to $\pm\alpha_1$, $OP_2$ will correspond to $\pm\alpha_2$, and so on.

Furthermore, the shape of the treatment radiation beam may be shaped by beam shaping device 80 (e.g., MLC leaves) at each OP. Also, the amount of dose of radiation to be delivered at each OP is modified and/or optimized based on the number of OPs and the radiation to be delivered to the patient area. The optimization may be done so that an aggregate of all OPs results in an optimum treatment plan.

In some aspects, a radiation therapy plan incorporates the constraint that the time between two consecutive OPs is equal to a nominal time between two consecutive breaths. For example, if the nominal time between two consecutive breaths is 6 seconds, then the planning system will optimize the treatment plan such that the radiotherapy gantry will take 6 seconds to travel from one OP to a next OP. In some aspects, a treatment planning clinician or other personnel examines the plan quality and decides if that is to be delivered to the patient.

In some embodiments, a radiotherapy treatment planning professional may enter a radiotherapy prescription into a planning system that specifies the amount of dose radiation a targeted patient area should receive. The treatment plan may also specify a maximum dose of radiation that the organs at risk (OAR) are allowed to receive. Additional considerations and constraints of the treatment plan may also be specified or otherwise entered and included in the treatment plan planning system, as done in an inverse-planning system that may be used to create an optimum IMRT (intensity-modulated radiation therapy) plan.

In accordance with some aspects of the rotational radiation treatment of moving targets herein, a planning system assumes the delivery of the radiation treatment is to be done by a continuously moving gantry 115. However, gantry 115 is assumed to have an upper speed limit. The speed limitations of gantry 115 movement may be specified to the planning system. Other operating limitations or constraints of the beam shaping device 80, such as MLC leaf speed, may also be provided to the planning system. Furthermore, the prescribed dose rate and a specific period of time for delivering the treatment radiation may be provided to the planning system. Based on such provided and specified information, the planning system may create an optimum plan for rotational radiation treatment of a moving patient area.

Based on a treatment plan considering at least some of the above discussed factors, radiotherapy system 100, including processor 175, may analyze the treatment plan to determine a gantry speed for moving gantry 115 along gantry movement arc 405 between adjacent and consecutive CPs. The gantry speed between two adjacent and consecutive CPs during which a beam shaping device is to be configured to accommodate delivery of a dose of treatment radiation may be determined such that beam shaping device 80 will reach a desired shape for delivery of a prescribed radiation treatment as gantry 115 travels between the two CPs. Such a determination of the gantry speed may consider the amount of leaf (i.e., 82/84 and 86/88) travels needed to obtain the desired beam shaping configuration and the effective leaf speed. The gantry speed between two adjacent and consecutive CPs during which a dose of radiation will be delivered may be determined such that a prescribed dose amount of radiation may be delivered to a patient area given the effective dose rate and the angular interval between the CPs.

Referring to FIG. 4, beam shaping device is dynamically configured between CP0 and CP1 at 410, CP2 and CP3 at 415, CP4 and CP5 at 420, and CP6 and CP7 at 425. During these intervals of movement, the speed of gantry 115 is adjusted such that beam shaping device 80 will reach the desired shape for delivery of a prescribed radiation treatment as gantry 115 travels between the two adjacent and consecutive CPs. Still referring to FIG. 4, a dose of radiation treatment is delivered to a patient area dynamically between CP1 and CP2 at 430, CP3 and CP4 at 435, and CP5 and CP6 at 440. During these intervals of movement, the speed of gantry 115 is adjusted such the prescribed dose amount of radiation may be delivered to the patient area given the effective dose rate and the angular interval between the CPs.

In some embodiments, a rate of dose delivery may change depending on the amount of dose that is to be delivered at each segment or at each OP±α. In some aspects, the dose rate will be set high to reduce treatment time for larger monitor unit (MU) values. For small MU values, the dose rate may be reduced to ensure accurate dose delivery, even though such a reduction of the dose rate may be achieved at some expense of a treatment time. In some aspects, and in an effort to reduce a treatment time, the radiation dose may be delivered in minimum amount of time (i.e., with maximum allowable dose rate).

With respect to the rotational radiation treatment of moving targets illustrated in FIG. 4 and discussed in regard to other embodiments herein, the delivery methodology of the treatment radiation may be referred to as a "burst mode" since the doses of radiation are delivered to the targeted patient area in "bursts" (i.e., at discrete intervals of gantry movement 405).

The "burst mode" of rotational radiation treatment of moving targets herein is well-suited to the treatment of targets having a periodic motion like, for example, breathing. In particular, when the time interval for dose delivery is sufficiently short, the moving target may effectively appear to be static. Accordingly, the treatment radiation may be accurately delivered to a targeted patient area.

With reference to FIG. 4, though not limited thereto, a treatment plan may specify, as an example, a rotational radiotherapy treatment including 36 OPs and an expected overall delivery of between 2 and 3 minutes. Accordingly, an average time of gantry travel from one OP to a next adjacent and consecutive OP will be about 4-5 seconds. In some aspects, it is noted that an average breathing cycle of a human is about once every 6 seconds, with some patients (e.g., sick or ill patients) typically exhibiting faster breathing on the order of about 4-5 seconds. Thus, it is noted that the gantry travel time from one CP to an adjacent CP is about equal to the typical time interval between consecutive breaths for this exemplary treatment plan. The rotational radiotherapy treatment planning and delivery scheme of embodiments herein also facilitates modulation of the gantry speed so that the gantry travel time may be brought into phase (i.e., synchronized) with the breathing cycle of the patient.

Figure 5:
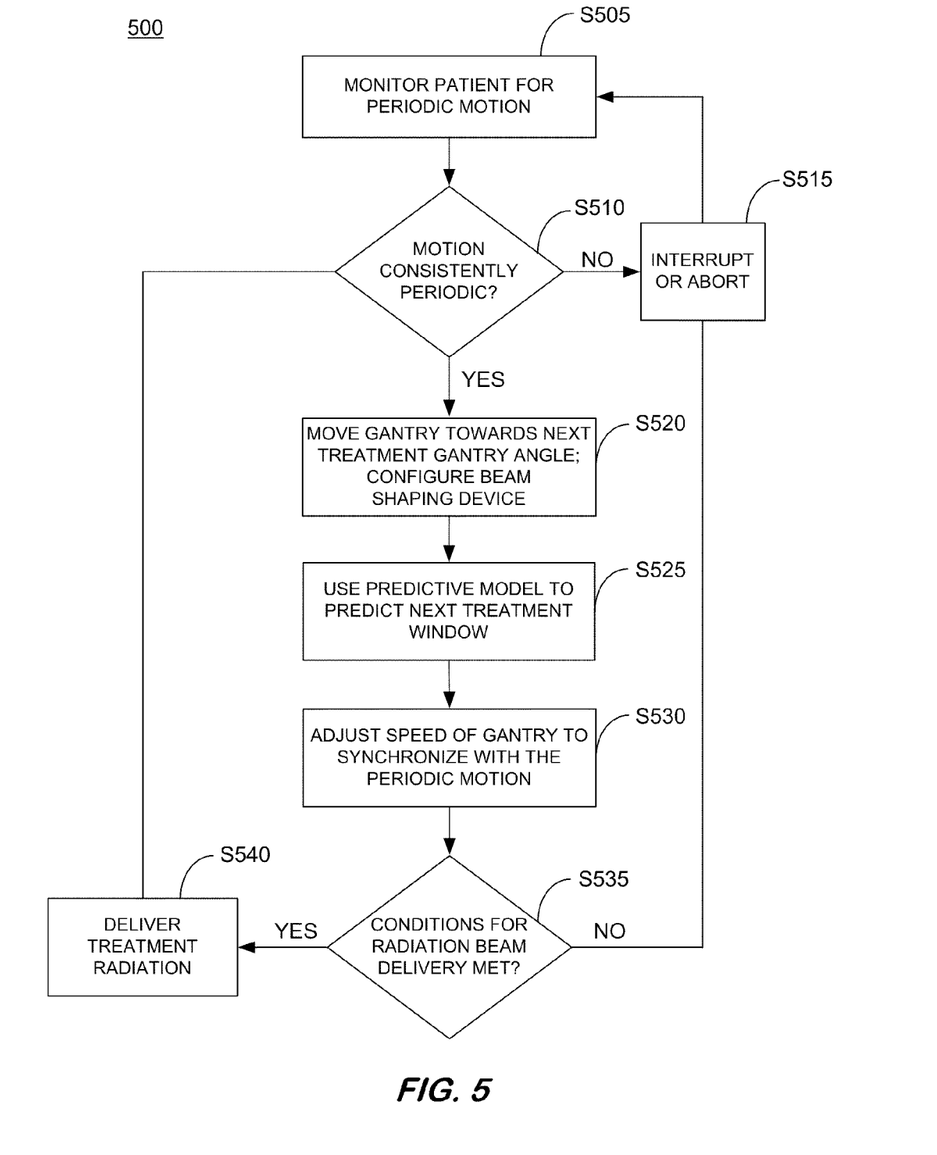
FIG. 5 is a flow diagram according to some embodiments.

FIG. 5 is a flow diagram of a process 500 to provide rotational radiation treatment of moving targets according to some embodiments. Process 500 and the other processes described herein may be performed using any suitable combination of hardware, software or manual means. Software embodying these processes may be stored by any medium, including a fixed disk, a floppy disk, a CD-ROM, a DVD-ROM, a optical disk, a magnetic tape, a solid state storage device, or a signal. Examples of these processes will be described below with respect to the elements of radiotherapy treatment room 100, but embodiments are not limited thereto.

In some embodiments, and prior to S505, an operator may interact with input device 165 of operator console 160 to initiate operation of linear accelerator 105 to receive and/or execute a radiotherapy treatment plan. In response to the user interaction, processor 175 may execute program code or instructions of a system control application stored in storage 180. The operator may further operate input device 165 to initiate radiation of a patient area (e.g., a tumor) of patient 150, including moving patient areas. Some aspects of the initiation may include positioning patient 150, gantry 115, and imaging device 135 at a position and angle for treatment, according to a treatment plan.

At S505, with the patient, gantry, and imaging device at a position and angle for treatment, a patient area of patient 150 is monitored for a periodic motion. In some aspects, the periodic or otherwise deterministic motion may be induced or related to a breathing function of patient 150. The monitoring of the patient area for the periodic motion may be performed by one or more methods and processes disclosed herein, but embodiments are not limited thereto.

At S510, a determination is made whether the monitored motion of the patient area is consistently periodic. If so, then process 500 continues to S520. In the instance the motion of the patient area is not consistently periodic, then process 500 continues to S515. For example, patient 150 may not be breathing in a consistent manner for any number of reasons. Under such circumstances, process 500 may be either interrupted or aborted. In the event the present process is aborted, flow 500 terminates at S515. In the instance the present process is interrupted, process 500 may resume at some future time at S505.

Continuing to S520, gantry 115 is moved towards a next treatment gantry angle (i.e., a OP). The next treatment gantry angle is specified in the treatment plan that is being implemented by radiotherapy system 100. Additionally, beam shaping device 80 is configured to a shape corresponding to the next treatment gantry angle. That is, gantry 115 is moved towards the next treatment gantry angle and beam shaping device 80 is adjusted, as needed, to shape a treatment radiation beam as prescribed for the dose delivery at the next treatment gantry angle.

At S525, a predictive model is used to estimate or otherwise predict when a next treatment window is to begin. The treatment window is a period of time designated for delivery of a treatment radiation beam to the patient area according to the treatment plan. The predictive model may be derived from the breathing pattern of patient 150 using on one or more mathematical methods, techniques, and algorithms. The present disclosure however is not limited to any one or more schemes, methods, techniques, and algorithms for determining the predictive model used to predict the occurrence of the next treatment window.

At S530, a speed of gantry 115 may be adjusted to synchronize the movement of gantry 115 with the periodic (breathing) motion of patient 150. In some aspects, the speed of continuously moving gantry 115 may be reduced if the monitored motion of the patient area is slower than a nominal value. The nominal value of the periodic motion may be specified in the treatment plan. In the instance the monitored motion of the patient area is slower than the nominal value, the speed of moving gantry 115 is reduced so that gantry 115 reaches the next OP during the predicted next treatment window. Radiotherapy system 100, including processor 175 may determine and/or execute the appropriate gantry speed adjustment.

In some instances when the next treatment window is predicted to approach faster than a nominal value (e.g., due to faster breathing), radiotherapy system 100, including processor 175, may make the appropriate gantry speed adjustment such that a dose of treatment radiation is not delivered in the next treatment window. In some instances the speed of continuously moving gantry 115 may be increased to deliever the treatment radiation in the next treatment window. The next treatment window may be skipped in an instance increasing the speed of continuously moving gantry 115 will exceed a speed limitation and/or compromise an accuracy of the delivery of the treatment radiation. In some embodiments, one or more upcoming treatment windows may be skipped until the next OP will occur in a treatment window.

At S535, a number of conditions or criteria may be evaluated to determine whether a treatment radiation beam will be delivered to the patient area in a "burst" mode, in accordance with aspects herein. For example, one or more determinations may be made, including but not limited to, a determination of whether the beam shaping device 80 has achieved the configuration required for delivery of the prescribed dose of treatment radiation; a determination may of whether gantry 115 is at the next treatment angle (i.e., OP) required for delivery of the prescribed dose of treatment radiation; and a determination of whether the "burst" of radiation will occur in the next treatment window.

In the instance the one or more conditions are satisfactorily met at S535, flow continues to S540 for delivery of the treatment radiation, in the dose prescribed by the treatment plan.

In the instance the one or more conditions are not satisfactorily met at S535, flow continues to S515, where the process is either interrupted or aborted. In some embodiments, resumption of an interrupted treatment delivery herein may consider a remaining undelivered portion of the treatment plan as a therapy session and resume the treatment at the point the radiotherapy was previously interrupted.

At the conclusion of S540, process 500 may continue with the rotational radiation treatment herein and as prescribed by the treatment plan by returning to S520 to move gantry 115 towards a next treatment gantry angle (i.e., OP). Process flow 500 may continue in this manner until gantry 115 has traversed all of the OPs and delivered the treatment radiation as specified in the treatment plan.

Figure 6:
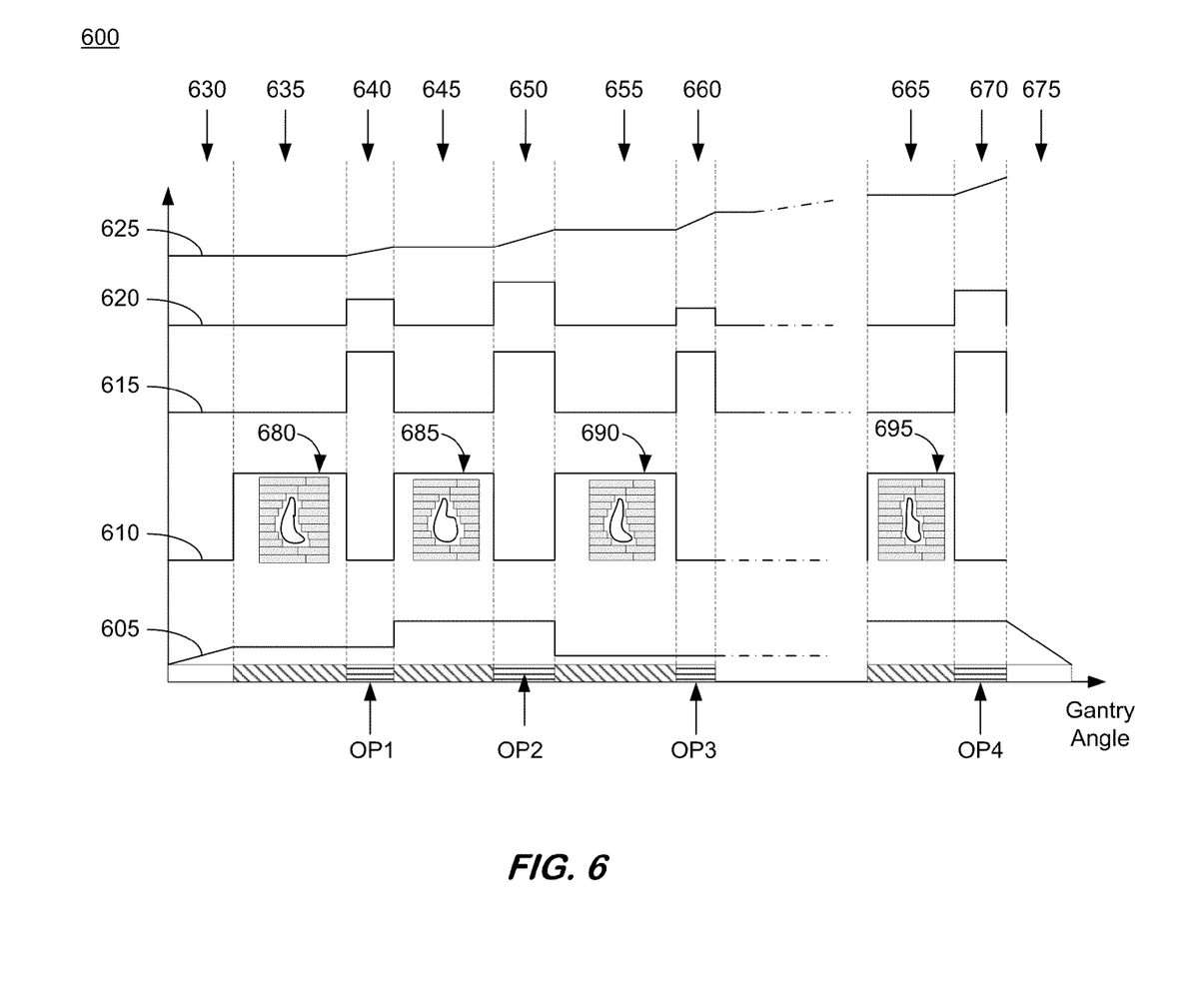
FIG. 6 is a timing diagram according to some embodiments.

FIG. 6 is a timing diagram 600 according to some embodiments. Gantry speed is shown at 605, beam shaping device motion is shown at 610, radiation delivery is shown at 615, a dose rate is shown at 620, and an accumulate dose is depicted at 625. As illustrated, gantry 115 ramps up at time period 630 and ramps down at time period 675. Further illustrated are the time periods during which beam shaping device 80 is moved, adjusted, or otherwise configured to a shape required for an upcoming delivery of treatment radiation. These beam shaping movements occur in time periods or intervals 635, 645, 655, and 665. As depicted at 680, 685, 690, and 695, beam shaping device 80 is dynamically adjusted per the treatment plan to accommodate the different patient areas or volumes presented at the different OPs. FIG. 6 also shows gantry 115 continuously moves after ramping up and before ramping down.

Further illustrated in timing diagram 600 are the time periods during which treatment radiation is delivered to a moving patient area. These periods of treatment radiation delivery occur in time periods or intervals 640, 650, 660, and 670. It is noted that the treatment radiation is delivered between two adjacent and consecutive CPs and at/around an OP located between the two adjacent and consecutive CPs.

Figure 7:
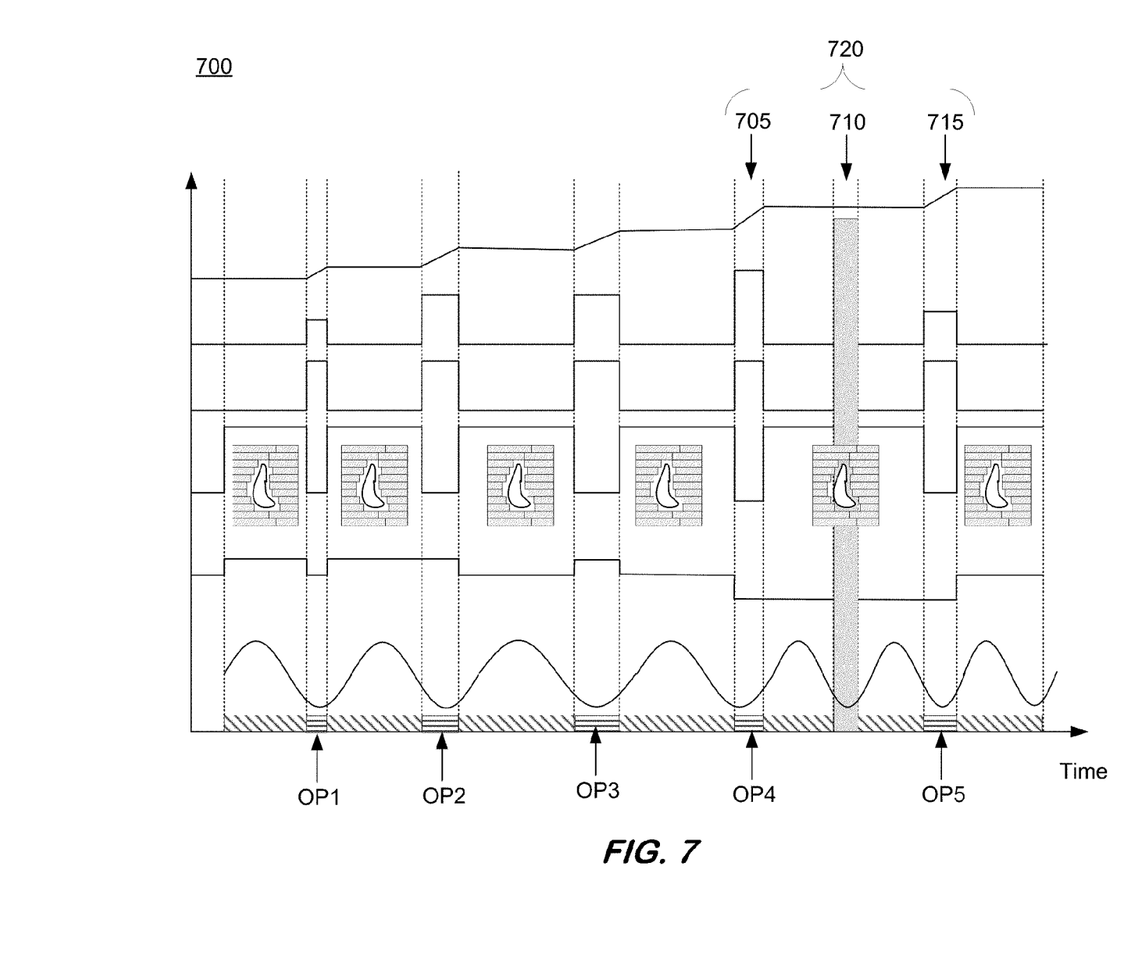
FIG. 7 is timing diagram according to some embodiments.

FIG. 7 is timing diagram according to some embodiments. While similar in many respects to timing diagram 600, timing diagram 700 also illustrates a delaying of treatment in response to a fluctuation in the breathing of patient 150. In particular, the breathing by patient 150 increases at region 720. In response to the increased rate of breathing, treatment radiation is not delivered during the next treatment window 710 after treatment window 705 but is instead delayed to until a future treatment window 715 presents itself. An adjustment to the speed of gantry 115 and/or timing of the delivery of the treatment radiation to the patient area is consistent with process 500, but not limited thereto.

The several embodiments described herein are solely for the purpose of illustration. Therefore, persons in the art will recognize from this description that other embodiments may be practiced with various modifications and alterations.

What is claimed is:

1. A method comprising:
   determining that a motion of a patient area of a patient due to breathing is substantially periodic according to a treatment plan, wherein the treatment plan specifies a first treatment gantry angle at which a prescribed dose of radiation is to be delivered, a nominal time between consecutive breathes of the patient, and a gantry travel time during which a radiotherapy beam shaping device is configured for delivery of the prescribed dose of radiation and is equal to the nominal time between consecutive breathes of the patient;
   moving a radiotherapy gantry towards the first treatment gantry angle;

moving the radiotherapy beam shaping device towards a first treatment shape corresponding to the first treatment gantry angle according to the treatment plan;

determining when a next treatment window is to begin based on a predictive model derived from the motion of the patient area, the treatment window being a period of time designated for delivery of a treatment radiation beam to the patient area according to the treatment plan;

adjusting the moving of the radiotherapy gantry such that the radiotherapy gantry will reach the first treatment angle during the determined next treatment window; and delivering a treatment radiation beam to the patient area during the determined next treatment window, wherein the radiotherapy gantry is at the first treatment gantry angle and the radiotherapy shaping device is configured to the first treatment shape.

2. The method of claim 1, wherein the radiotherapy gantry is continuously moving.

3. The method of claim 1, further comprising receiving the treatment plan.

4. The method of claim 1, wherein a speed of the moving of the radiotherapy gantry towards the first treatment gantry angle depends, at least in part, on a rate at which the radiotherapy beam shaping device can be configured to the first treatment shape.

5. The method of claim 1, further comprising:
determining that the radiotherapy beam shaping device is configured to the first treatment shape corresponding to the first treatment gantry angle;
determining that the radiotherapy gantry has reached the first treatment gantry angle according to the treatment plan; and
determining that the radiotherapy gantry will reach the first treatment angle during the determined next treatment window.

6. The method of claim 1, further comprising:
modulating a rate of dose delivery of the treatment radiation beam depending on the prescribed dose of radiation to be delivered at the first treatment gantry angle.

7. The method of claim 1, wherein the treatment radiation beam is delivered with a maximum allowable dose rate, according to the treatment plan.

8. The method of claim 1, wherein the treatment window corresponds to a prescribed time interval of the patient's breathing cycle, according to the treatment plan.

9. The method of claim 1, further comprising:
determining that the motion of the patient area of the patient due to breathing is substantially periodic according to the treatment plan, wherein the treatment plan specifies a second treatment gantry angle at which a prescribed dose of radiation is to be delivered, a nominal time between consecutive breathes of the patient, and a gantry travel time during which a radiotherapy beam shaping device is configured for delivery of a prescribed dose of radiation and is equal to the nominal time between consecutive breathes of the patient;
moving the radiotherapy gantry towards a second treatment gantry angle;
moving the radiotherapy beam shaping device towards a second treatment shape corresponding to the second treatment gantry angle;
determining when a second next treatment window is to begin based on a predictive model derived from the motion of the patient area;
adjusting the moving of the radiotherapy gantry such that the radiotherapy gantry will reach the second treatment angle during the determined second next treatment window; and
delivering a treatment radiation beam to the patient area during the determined second next treatment window, wherein the radiotherapy gantry is at the second treatment gantry angle and the radiotherapy shaping device is configured to the second treatment shape.

10. A system comprising:
a rotatable radiotherapy gantry;
an emission device mounted to the radiotherapy gantry to emit a treatment radiation beam;
a radiotherapy beam shaping device; and
a processor to:
determine that a motion of a patient area of a patient due to breathing is substantially periodic according to a treatment plan, wherein the treatment plan specifies a first treatment gantry angle at which a prescribed dose of radiation is to be delivered, a nominal time between consecutive breathes of the patient, and a gantry travel time during which a radiotherapy beam shaping device is configured for delivery of the prescribed dose of radiation and is equal to the nominal time between consecutive breathes of the patient;
move the radiotherapy gantry towards the first treatment gantry angle;
move the radiotherapy beam shaping device towards a first treatment shape corresponding to the first treatment gantry angle according to the treatment plan;
determine when a next treatment window is to begin based on a predictive model derived from the motion of the patient area, the treatment window being a period of time designated for delivery of a treatment radiation beam to the patient area according to the treatment plan;
adjust the moving of the radiotherapy gantry such that the radiotherapy gantry will reach the first treatment angle during the determined next treatment window; and
deliver a treatment radiation beam from the emission device to the patient area during the determined next treatment window, wherein the radiotherapy gantry is at the first treatment gantry angle and the radiotherapy shaping device is configured to the first treatment shape.

11. The system of claim 10, wherein the radiotherapy gantry is continuously moving during an execution of the treatment plan.

12. The system of claim 10, further comprising the processor to receive the treatment plan.

13. The system of claim 10, wherein a speed of the moving of the radiotherapy gantry towards the first treatment gantry angle depends, at least in part, on a rate at which the radiotherapy beam shaping device can be configured to the first treatment shape.

14. The system of claim 10, further comprising the processor to:
determine that the radiotherapy beam shaping device is configured to the first treatment shape corresponding to the first treatment gantry angle;
determine that the radiotherapy gantry has reached the first treatment gantry angle according to the treatment plan; and
determine that the radiotherapy gantry will reach the first treatment angle during the determined next treatment window.

15. The system of claim 10, further comprising the processor to modulate a rate of dose delivery of the treatment radiation beam depending on the prescribed dose of radiation to be delivered at the first treatment gantry angle.

16. The system of claim 10, wherein the treatment radiation beam is delivered with a maximum allowable dose rate, according to the treatment plan.

17. The system of claim 10, wherein the treatment window corresponds to a prescribed time interval of the patient's breathing cycle, according to the treatment plan.

18. The system of claim 10, further comprising the processor to:
   determine that the motion of the patient area of the patient due to breathing is substantially periodic according to the treatment plan, wherein the treatment plan specifies a second treatment gantry angle at which a prescribed dose of radiation is to be delivered, a nominal time between consecutive breathes of the patient, and a gantry travel time during which a radiotherapy beam shaping device is configured for delivery of a prescribed dose of radiation and is equal to the nominal time between consecutive breathes of the patient;
   move the radiotherapy gantry towards a second treatment gantry angle;
   move the radiotherapy beam shaping device towards a second treatment shape corresponding to the second treatment gantry angle;
   determine when a second next treatment window is to begin based on a predictive model derived from the motion of the patient area;
   adjust the moving of the radiotherapy gantry such that the radiotherapy gantry will reach the second treatment angle during the determined second next treatment window; and
   deliver a treatment radiation beam to the patient area during the determined second next treatment window, wherein the radiotherapy gantry is at the second treatment gantry angle and the radiotherapy shaping device is configured to the second treatment shape.

* * * * *